(12) United States Patent
Silvian et al.

(10) Patent No.: US 6,968,231 B1
(45) Date of Patent: Nov. 22, 2005

(54) HIGH VOLTAGE CONVERTER FOR AN IMPLANTABLE MEDICAL DEVICE

(75) Inventors: Sergiu Silvian, La Crescenta, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 497 days.

(21) Appl. No.: 10/052,812

(22) Filed: Jan. 18, 2002

(51) Int. Cl.[7] .............................................. A61N 1/378
(52) U.S. Cl. ........................................ 607/12; 607/4
(58) Field of Search ............................. 607/4, 5, 9, 12, 607/7

(56) References Cited

U.S. PATENT DOCUMENTS

| | | | |
|---|---|---|---|
| 4,595,009 A | * | 6/1986 | Leinders ........................ 607/5 |
| 4,830,006 A | * | 5/1989 | Haluska et al. ................. 607/4 |
| 5,466,254 A | | 11/1995 | Helland ...................... 607/123 |
| 5,620,464 A | * | 4/1997 | Kroll et al. ..................... 607/5 |
| 5,941,906 A | | 8/1999 | Barreras, Sr. et al. ........ 607/66 |
| 5,964,787 A | * | 10/1999 | Kerver et al. .................. 607/9 |
| 6,317,634 B1 | | 11/2001 | Lyden .......................... 607/29 |

* cited by examiner

Primary Examiner—George R. Evanisko

(57) ABSTRACT

A high voltage converter circuit for an implantable cardiac device. The circuit includes a plurality of transistors that are connected in parallel to a battery and the primary winding of a transformer. A switching element is connected to the circuit so as to periodically connect and disconnect the capacitors to the primary winding of the transformer to thereby induce the capacitors to be charged and periodically discharged across the transformer into charging capacitors. A circuit also preferably includes a disconnect circuit that will disconnect the capacitors from the battery during periods of non-use to inhibit unwanted dissipation of the battery's energy.

13 Claims, 3 Drawing Sheets

HIGH VOLTAGE CONVERTER FOR AN IMPLANTABLE MEDICAL DEVICE

FIELD OF THE INVENTION

The present invention relates to implantable medical devices and, in particular, concerns a high voltage converter used in implantable medical devices that is configured to reduce loss of battery power due to leaking capacitors.

BACKGROUND OF THE INVENTION

Implantable medical devices are devices that are implanted within the body of a patient so as to provide therapy to an organ of the patient. These types of devices have become increasingly common for the treatment of a variety of different medical ailments. For example, implantable cardiac stimulation devices, such as pacemakers and implantable cardioverter defibrillators (ICD's), have been in use for many years and provide electrical stimuli to the heart of the patient to regulate heart function. Similarly, neural stimulators are also now being implanted into patients' bodies in order to provide electrical stimulation to selected regions of the patient's brain to regulate brain function. Other medical devices can include devices for stimulating other organs or tissues, such as the pancreas, kidneys, etc.

Typically, an implantable medical device is equipped with a battery that supplies low voltage DC power to the implanted device. Generally, known low voltage batteries such as lithium, iodine, silver vanadium oxide (SVO) or lithium monofluoride batteries are used to provide power to the implantable device. Typically, these batteries provide output voltages in the range of 2 to 4 volts DC. However, it common for the implantable medical device to provide comparatively high voltage waveforms to an organ of the patient in order to regulate the organ's function.

For example, ICD's will often provide waveforms having peak voltage of approximately 800 volts or greater to the heart of a patient in order to terminate ventricular fibrillation. Similarly, neural stimulators will provide voltages in the range of 20 to 50 volts in order to terminate epileptic episodes. Hence, many implantable medical devices are equipped with a high voltage converter that uses the relatively low output voltage provided by the battery to develop a high voltage output signal that can be applied to one or more high voltage capacitors. When the capacitor(s) voltage reaches a programmed value, the charge stops and next the capacitor(s) voltage is applied to the organ of the patient using specialized HV switching means.

A typical high voltage converter used in implantable medical devices generally has a primary winding of a transformer being connected to the positive and negative plates of a battery via a switch, such as a transistor. One or more bypass capacitors are connected in parallel to the battery such that the bypass capacitors help maintain the voltage supplied to the transformer primary at a stable level during charging. A high voltage rectification circuit that includes one or more delivery capacitors is typically connected to the secondary winding of the transformer. Moreover, a switching network is generally attached to the switch such that the switch can be toggled at relatively high frequency. When the switch is turned on, an increasing current is provided to the primary winding of the transformer which stores energy as magnetic flux in the core of the transformer. When the switch is turned off, the stored energy is transferred from the core to the load via the secondary winding. Hence, by repeatedly cycling the switch at a relatively high frequency, energy can be transferred from the battery to the high voltage capacitors.

To improve the efficiency of this high voltage charging process, the bypass capacitors that are used are typically capacitors that have particularly low equivalent series resistance. Lower equivalent series resistance among the capacitors results in less of the battery's energy being dissipated in the form of heat in the resistance. Of course, in implanted medical devices, conservation of battery power is important as replacement of the battery often requires an invasive surgical procedure.

One common family of capacitors that is used as bypass capacitors in high voltage converter circuits for implantable medical devices is ceramic dielectric capacitors with a Y5V dielectric. Advantageously, ceramic capacitors are known to have particularly low equivalent series resistance and, thus, increases the efficiency of converter circuits.

One problem with ceramic capacitors is that these types of capacitors are typically not self-healing. In other words, if cracks develop in the ceramic dielectric, leakage currents will then flow from one plate of the capacitor to the other. This leakage current also represents an unwanted dissipation of the battery's energy and discharge it in a relatively short period. Typically, with the electrolytic capacitors that are also commonly used in implantable medical devices, leakage paths that develop between the plates as a result of applied voltages are often repaired by the electrolyte. Consequently, electrolytic capacitors have reduced leakage currents after an internal defect but, unfortunately, they also have a higher equivalent series resistance.

Hence, while ceramic capacitors are generally preferred to be used as the bypass capacitors in high voltage converter circuits for implantable medical devices, these ceramic capacitors also may produce leakage paths through which battery power can be dissipated when the bypass capacitors are not being charged. Again, dissipation of battery power is undesirable due to the difficulties associated with replacing batteries in implantable medical devices and also the consequences of battery failure in an implanted device. Hence, there is a need for a high voltage converter circuit for an implantable medical device that permits efficient charging of the HV capacitor but also reduces unwanted dissipation of battery power during the quiescent period of the high voltage converter circuit in an event of capacitors degradation. To this end, there is a need for a high voltage converter circuit for an implantable medical device with which high efficiency capacitors, such as ceramic capacitors, can be used as bypass capacitors while the effect of such leakage current that may occur with such types of capacitors can be reduced or eliminated.

SUMMARY OF THE INVENTION

The aforementioned needs are satisfied by the implantable medical device described herein which, in one aspect, comprises a device that delivers high voltage therapeutic stimulation to an organ of the patient. This device includes an implantable delivery device that delivers the therapeutic stimulation to the organ of the patient, a battery and a converter that is coupled to the battery and to the implantable delivery device. For the purpose of this description, a high voltage is defined as any voltage higher than the battery voltage. The converter includes at least one bypass capacitor that is selectively connected to the battery via a switching network and at least one delivery capacitor that is coupled to the implantable delivery circuit.

The device further includes a controller that induces the battery and the at least one bypass capacitor to be connected to the battery such that charge is accumulated in the bypass capacitor during a charging cycle and the controller further induces the at least one bypass capacitor and the battery to be periodically coupled to the delivery capacitor such that charge is accumulated in the delivery capacitor so as to develop a high voltage charge in the delivery capacitor for delivery of the high voltage therapeutic stimulation to the organ of the patient. The controller is further configured to disconnect at least one bypass capacitor from the battery after completion of the charging cycle to inhibit undesired dissipation of battery energy as a result of leakage currents during quiescent periods of the converter.

In one particular implementation, the bypass capacitors are connected to a primary winding of a transformer in series with a first switching element, such as a transistor, and the bypass capacitors are also connected to the battery via a second switching element, such as a transistor and a shunt resistor intended to sense the transformer primary current. The controller induces the delivery of an alternating signal, such as a square wave signal, to the first switching element, such that the battery and the bypass capacitors are selectively connected and disconnected to the primary winding of the transformer. In this way, a varying current is applied to the primary winding which results in a varying current being inductively induced on the secondary winding to thereby charge the delivery capacitors.

The circuit is further configured so as to deliver a substantially constant output signal to the second switching element whenever the alternating signal is being provided to the first switching element. When the controller is no longer providing the alternating signal to the first switching element, the second switching element is disabled which thereby disconnects the bypass capacitors from the battery. In this way, unwanted dissipation of battery energy as a result of leakage across the plurality of bypass capacitors is eliminated. While the HV converter is working, and this is only for a few seconds at a time, the additional leakage current is insignificant compared with the high current required for conversion.

In one particular implementation, the implantable medical device comprises an implantable cardiac stimulation device, such as an implantable cardioverter defibrillator (ICD). It will, of course, be appreciated, however, that the implantable medical device can comprise any of a number of implantable medical devices that need to apply an output voltage that is substantially greater than the voltage provided by the battery such that the output voltage must be developed using capacitors. The use of a circuit that selectively disconnects the bypass capacitors allows for the use of bypass capacitors, such as ceramic capacitors, which are more efficient due to their relatively low equivalent series resistance, but may otherwise generate leakage currents. These and other objects and advantages will become more apparent from the following description taken in conjunction with accompanying drawings.

BRIEF DESCRIPTION OF THE DRAWINGS

Further features and advantages of the device described herein may be more readily understood by reference to the following description taken in conjunction with the accompanying drawings, in which.

DETAILED DESCRIPTION OF THE PREFERRED EMBODIMENT

The following description is of the best mode presently contemplated. This description is not to be taken in a limiting sense but is made merely for the purpose of describing the general principles of the device. The scope of the invention should be ascertained with reference to the issued claims. In the description that follows, like numerals or reference designators will be used to refer to like parts or elements throughout.

Figure 1:
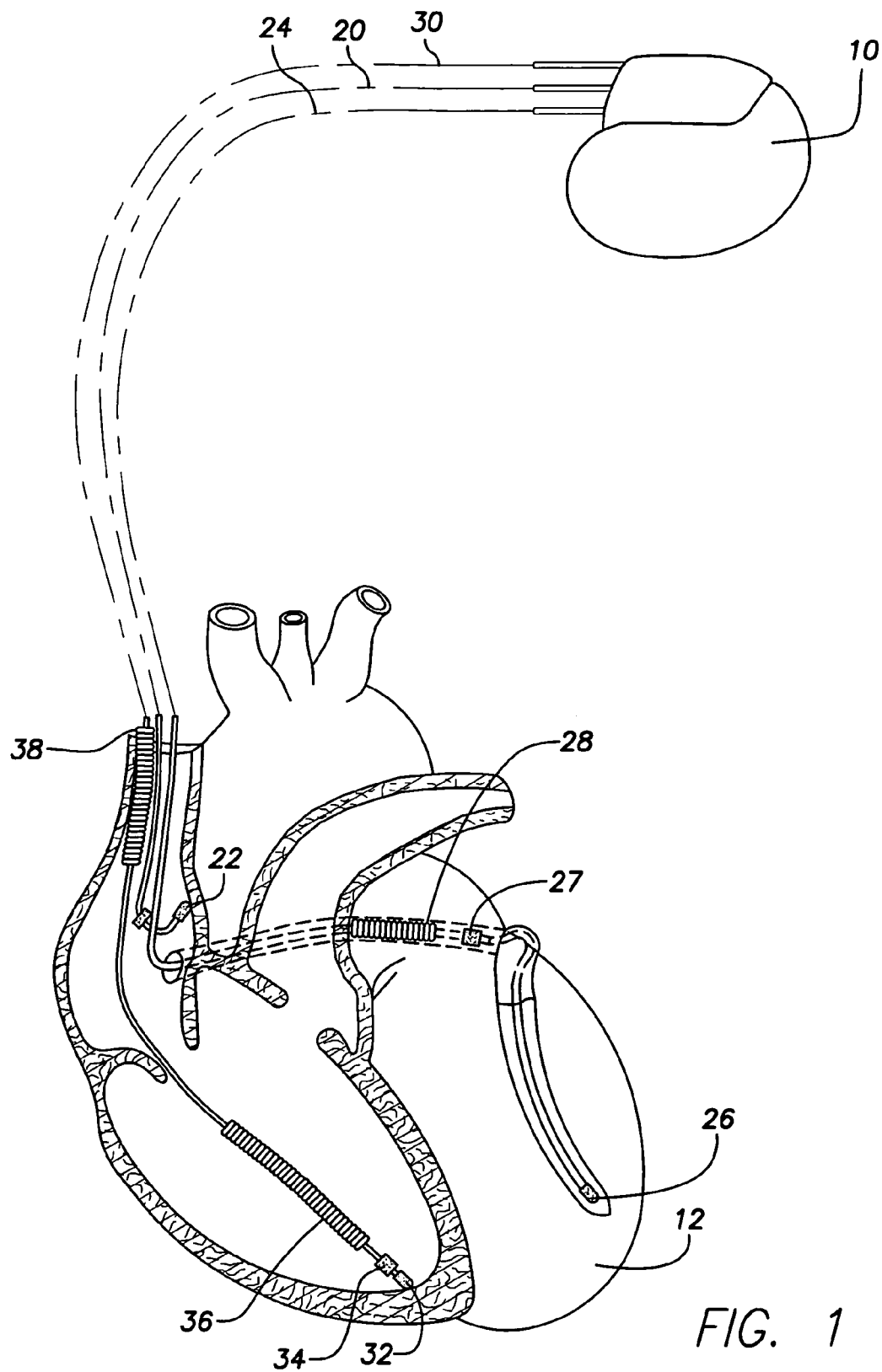
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
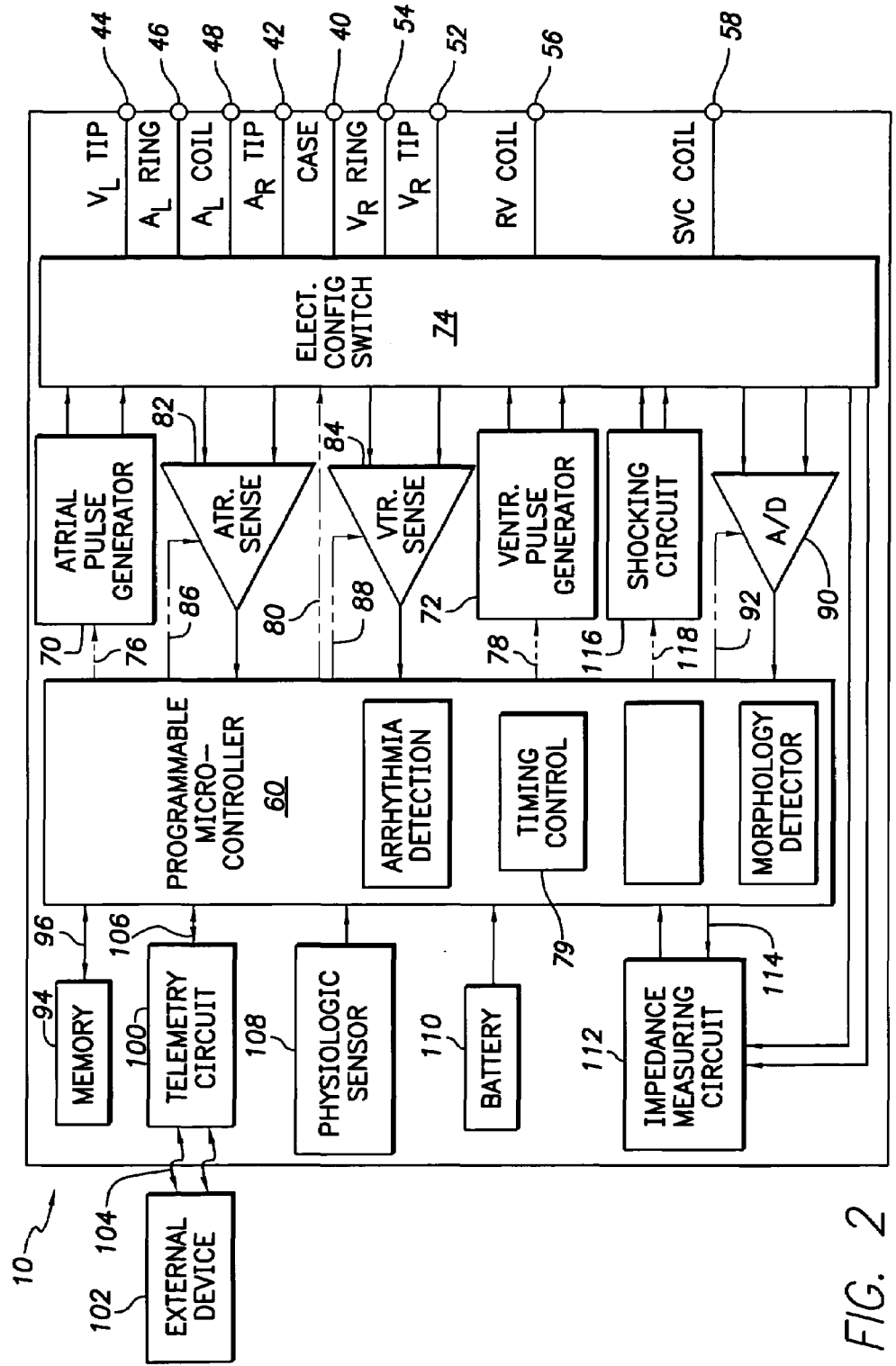
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an, impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
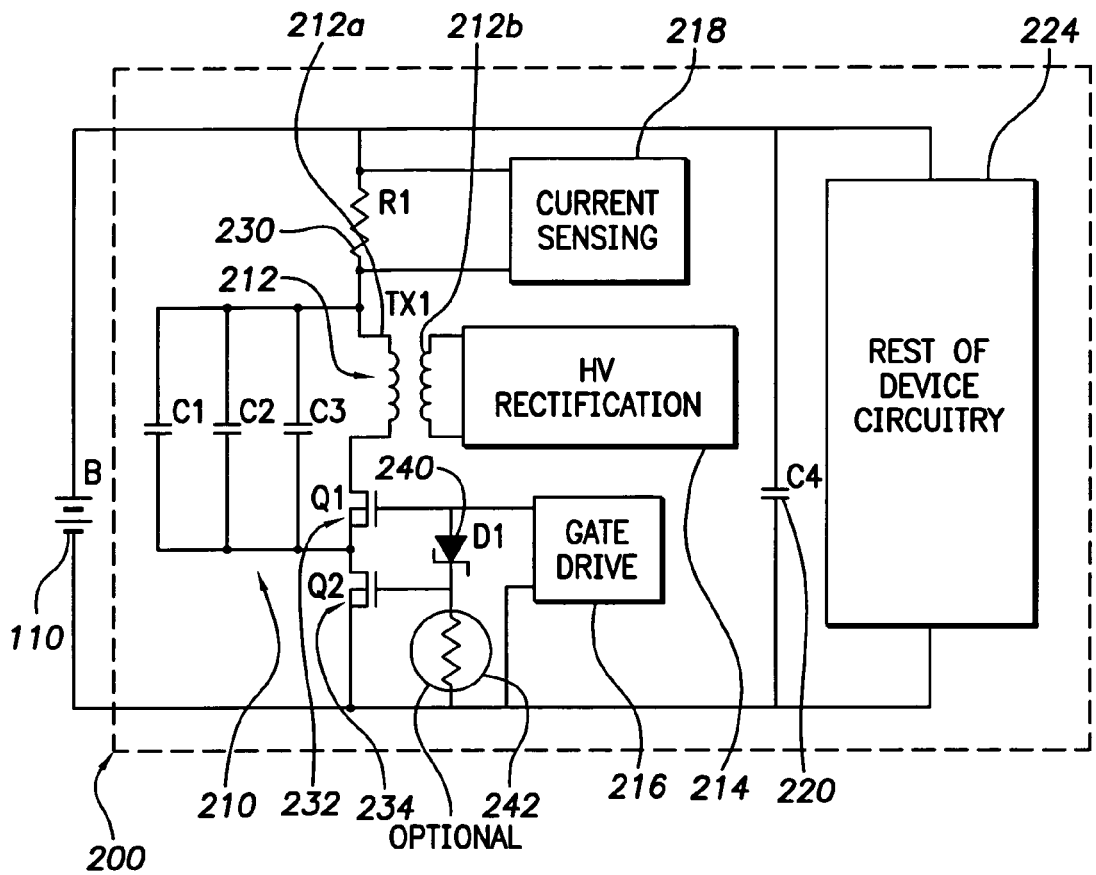
FIG. 3 is a schematic diagram of a high voltage converter circuit that is part of the shocking circuit of FIG. 2.

FIG. 3 is a block diagram illustrating a high voltage converter circuit 200 that, in this particular implementation, is part of the shocking circuit 116 of FIG. 2. As discussed above, the implantable cardiac stimulation device 10 includes the battery 110 that provides a low voltage output, e.g., on the order of 3 volts, and a shocking circuit 116 that provides a high voltage shock to the heart of the patient via the leads 20, 24, and 30. Consequently, the shocking circuit 116 must incorporate circuitry that will develop a high voltage, e.g., on the order of 150–800 volts, signal using the output voltage of the battery 110. As is illustrated in FIG. 3, the high voltage converter circuit 200 in this particular implementation includes a plurality of bypass capacitors 210, denoted C1–C3, that are generally connected in parallel with the battery 110 through a primary switch element Q2 and a current sensing resistor R1. The plurality of bypass capacitors are preferably ceramic capacitors with a Y5V dielectric. Typically, the plurality of these capacitors have a capacitance on the order of 20 to 50 microfarad. As is also illustrated in FIG. 3, the plurality of bypass capacitors 210 are connected across the primary winding 212a of a transformer 212 in series with a secondary switch element Q1, such that pulsed current drawn by the transformer 212 does not result in too high a voltage ripple on the battery voltage. Moreover, the primary winding of the transformer 212a is connected to the positive side of the battery 110 via a sensing resistor 230 denoted R! in FIG. 3. The primary winding 212a is also connected to the negative side of the battery 110 via a transistor 232, denoted Q1 in FIG. 3, and a transistor 234, denoted Q2 in FIG. 3.

The secondary winding 212b of the transformer 212 is then coupled to a high voltage rectification circuit 214 that will be described in greater detail in connection with FIG. 4. The gate of the transistor 232 is connected to a gate drive circuit 216 which is controlled by the programmable microcontroller 60 in the manner that will be described in greater detail below. Moreover, the gate of the transistor 234 is also connected to the output of the gate drive circuits 216 via a diode 240. As will be discussed below, the gate of the second transistor 234 can also be connected to the negative side of the battery 110 via an optional resistor 242.

As is also illustrated in FIG. 3, the sensing resistor 230 is preferably connected to a current sensing logic circuit 218 that is also controlled by the programmable microcontroller 60. As is understood, the current sensing circuit 218 samples the voltage at the resistor 230 in order to further regulate the charge current that is being supplied to the primary winding 212a of the transformer 212.

These components shown in FIG. 3 comprise the basic high voltage converter circuit 200 of the preferred embodiment. As is further illustrated in FIG. 3, the rest of the device circuitry 224 discussed above in connection with FIGS. 1 and 2, also receive power from the positive and negative sides of the battery 110 in a manner that is known in the art. Moreover, as is illustrated in FIG. 3, a decoupling capacitor 220, which in this embodiment comprises an electrolytic capacitor having a capacitance on the order of 10–30 microfarads is connected in parallel to the battery 110 such that a substantially low voltage ripple DC voltage can be provided to the rest of the device circuitry 224 without being substantially affected by the operation of the high voltage converter circuit 200.

The high voltage converter 200 is endeavoring to charge one or more delivery capacitors to a relatively high level of voltage such that the delivery capacitors can then provide a high voltage output waveform to the patient's body in the above-described manner. In order to charge the high voltage delivery capacitors, the programmable microcontroller 60, via the gate drive circuit 216, provides a high frequency square wave signal to the gate of the transistor 232. As a result of the diode 240 and the intrinsic transistor 234 gate-source capacitance, the high frequency square wave signal that is being provided to the gate of the transistor 232 is rectified into a positive output voltage on the transistor 234 gate. Consequently, the transistor 234 is then turned continuously on, but the transistor 232 is turned on and off at a high frequency, e.g., on the order of 50 to 250 kHz.

Hence, when the charging cycle is initiated, e.g., the high frequency signal and the constant signal are being provided to the transistors 232, 234 respectively, the bypass capacitors 210 are continuously connected to the battery 110 and can therefore provide a reservoir of change to the transformer 212 during charging of the primary winding and further provide high frequency filtering.

Charge is transferred via the HV rectification circuit 214 across the windings 212b in the following manner. When the high frequency signal to the transistor 232 is high, the winding 212a is connected across both the battery and the bypass capacitors 210 and receives charge from both these sources. This results in a changing current in the primary winding 212a. When transistor 232 is controlled off, the stored energy in the transformer generates a secondary current in the secondary winding 212b. The current in the secondary winding is rectified by the HV rectification circuit 214 and charges delivery capacitors in a manner that will be described in greater detail hereinbelow. These on off cycles repeat at high frequency until the controller determines that the voltage on 220 is equal to the program voltage, when it stops driving the transistor 232 on and leaving it with a gate voltage close to zero. After converter is in this way turned off, the gate voltage on the transistor 234 slowly discharges to zero through the reverse leakage of Shottky diode 240. After a second or so, the 234 gate voltage reaches zero and 234 switches off separating the bypass capacitors 210 from the battery. A resistor 242 of 10 Mohm can provide additional leakage to speed up this process if required.

As discussed above, the bypass capacitors 210 are preferably ceramic capacitors with Y5V dielectric and as explained earlier they can become leaky. However, as is shown in FIG. 3, the gate drive circuit 216 only connects the bottom plate of the bypass capacitors 210 to the negative pole of the battery 110 when the high frequency signal is being applied to the transistor 232. Hence, the bypass capacitors 210 are only connected to the battery 110 when the HV converter is actually operating, i.e., the high frequency switching signal is being provided to the transistor 232. In this way, battery power is inhibited from leaking across the plates of the bypass capacitors during quiescent periods of the converter circuit.

More specifically, when the microcontroller 60 disables the gate drive 216 such that it is no longer providing the high frequency signal to the transistor 232, the voltage being applied to the gate of the transistor 234 goes low thereby creating a substantially open circuit between the bottom plates of the bypass capacitors 210 and the negative pole of the battery 110 which thereby inhibits undesirable leakage of the battery 110. As is further illustrated in FIG. 3, an optional resistor 242 can also be interposed between the gate of the transistor 232 and the negative pole of the battery 110 such that, when the gate drive circuit 216 stops producing the high frequency square wave signal, the voltage on the gate of the transistor 234 can be pulled low, thereby hastening the turning off of the transistor 234 and the disconnecting of the bypass capacitors 210 from the battery 110.

Figure 4:
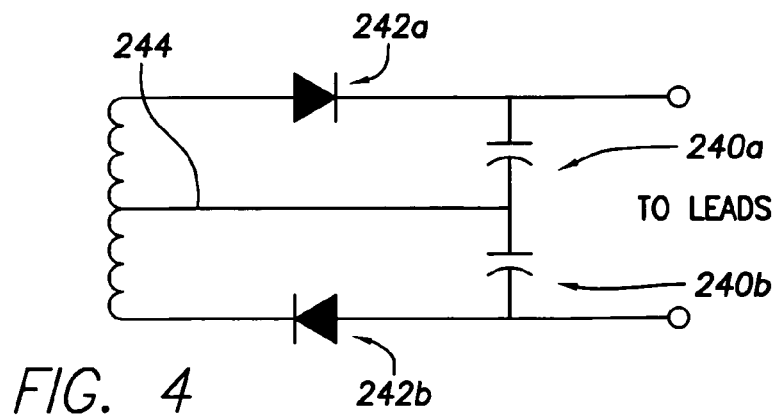
FIG. 4 is an exemplary schematic of the high voltage discharge capacitor that is part of the shocking circuit of FIG. 2.

FIG. 4 is a simplified schematic illustrating the high voltage rectification circuit 214. As is illustrated, the secondary winding 212b is connected to delivery capacitors 240a, 240b via rectifying diodes 242a, 242b using a well known rectification circuit.

The delivery capacitors 240a, 240b, receive charge via the secondary winding 212b and build up sufficient charge that a high voltage waveform can be delivered. In some implementations, the storage capacitors 240a, 240b are capable of delivering a waveform having a voltage in excess of 800 volts.

While the device has been described in connection with a particular embodiment associated with an implantable cardiac stimulation device, it will be appreciated that any implantable medical device that requires the development of high voltage signals can use the high voltage converter circuit of the illustrated embodiment. For example, the converter can also be used in an implantable medical device such as a neural stimulator like the stimulator disclosed in U.S. Pat. No. 5,941,906 which is hereby incorporated by reference in its entirety.

Hence, although the foregoing description of the preferred embodiments has shown, described and pointed out the fundamental novel features of the device, it will be understood that various omissions, substitutions, and changes in the form of the detail of the apparatus as illustrated as well as the uses thereof, may be made by those skilled in the art without departing from the spirit of the present invention. Consequently, the scope of the invention should not be limited to the foregoing discussion, but should be defined by the appended claims.

What is claimed is:

1. An implantable medical device that delivers high voltage therapeutic signals to an organ of a patient, the device comprising:
   an implantable delivery device that delivers the high voltage therapeutic signals to the organ of the patient;
   a battery;
   a converter coupled to the battery and to the implantable delivery device wherein the converter comprises at least one bypass capacitor and a switching network, wherein the at least one bypass capacitor is selectively connected to the battery via the switching network, wherein the converter further comprises at least one delivery capacitor that is coupled to the implantable delivery device;

a controller that induces the converter to change between a quiescent period and a charging cycle wherein the at least one bypass capacitor is connected to the battery during the charging cycle such that charge is accumulated in the bypass capacitor, wherein the delivery capacitor is also charged during the charging cycle based on the charge in the at least one bypass capacitor, and wherein the controller further controls the converter to disconnect the at least one bypass capacitor from the battery after completion of the charging cycle to reduce undesired dissipation of battery energy as a result of leakage currents during the quiescent period of the converter;

wherein the converter comprises a transformer having a primary winding and a secondary winding wherein the switching network periodically connects the battery and the at least one bypass capacitor to the primary winding of the transformer so as to produce changing current in the primary winding that results in inductively induced changing current in the secondary winding and wherein the at least one delivery capacitor is connected to the secondary winding of the transformer such that the changing current results in the delivery of charge to the at least one delivery capacitor;

wherein the switching network comprises a first switching element that is interposed between the at least one bypass capacitor, the battery and the primary winding of the transformer and wherein the controller induces the delivery of a high frequency signal to the first switching element so as to periodically connect the at least one bypass capacitor and the battery in parallel to the primary winding of the transformer;

wherein the switching network further comprises a second switching element that connects the at least one bypass capacitor to the battery wherein the controller induces the second switching element to disconnect the at least one bypass capacitor from the battery during the quiescent periods of the converter;

wherein the first and second switching elements comprise transistors having gates and wherein the controller applies an oscillating signal to the first transistor; and a rectifying element that is interposed between the source of the oscillating signal and the second transistor such that when the oscillating signal is produced, the second transistor receives a substantially constant input voltage that turns on the transistor.

2. An implantable cardiac stimulation device comprising:

at least one lead adapted to be positioned adjacent the heart of the patient to thereby permit delivery of a high voltage therapeutic signal;

a battery that produces a low voltage output;

a converter that comprises at least one bypass capacitor and at least one delivery capacitor wherein the converter in a charging cycle receives the low voltage output of the battery and charges the at least one bypass capacitor and wherein charge is periodically delivered to the at least one delivery capacitor during the charging cycle such that the at least one delivery capacitor is charged to be able to deliver the high voltage therapeutic signal;

a controller that determines the state of charge of the at least one delivery capacitor and induces the converter to enter the charging cycle when the controller determines that the at least one delivery capacitor is in need of charge to be able to deliver the high voltage therapeutic signal and wherein the controller disconnects the at least one bypass capacitor from the battery when the controller determines that the at least one delivery capacitor is not in need of charge to thereby inhibit undesired dissipation of battery energy as a result of leakage currents in the at least one bypass capacitor;

wherein the converter comprises a transformer having a primary winding and a secondary winding wherein the battery and the at least one bypass capacitor are periodically connected to the primary winding of the transformer so as to produce changing current in the primary winding that results in inductively induced changing current in the secondary winding and wherein the at least one delivery capacitor is connected to the secondary winding of the transformer such that the changing current results in the delivery of charge to the at least one delivery capacitor;

wherein the converter comprises a first switching element that is interposed between the at least one bypass capacitor, the battery and the primary winding of the transformer and wherein the controller induces the delivery of an alternating signal to the first switching element so as to periodically connect the at least one bypass capacitor and the battery to the primary winding of the transformer;

wherein the converter further comprises a second switching element that connects the at least one bypass capacitor to the battery wherein the controller induces the second switching element to disconnect the at least one bypass capacitor from the battery when the converter is not in the charging cycle;

wherein the first and second switching elements comprise transistors and wherein the controller induces the application of the alternating signal to the first transistor; and a rectifying element that is interposed between the source of the alternating signal and the second transistor such that when the alternating signal is produced, the second transistor receive a substantially constant input voltage that turns on the second transistor.

3. An implantable medical device that delivers high voltage therapeutic signals to an organ of a patient, the device comprising:

an implantable delivery device that delivers the high voltage therapeutic signals to the organ of the patient;

a battery;

a converter coupled to the battery and to the implantable delivery device wherein the converter comprises at least one bypass capacitor and a switching network, wherein the at least one bypass capacitor is selectively connected to the battery via the switching network, wherein the at least one bypass capacitor has a capacitance on the order of 20–50 microfarads, and wherein the converter further comprises at least one delivery capacitor that is coupled to the implantable delivery device;

a controller that induces the converter to change between a quiescent period and a charging cycle wherein the at least one bypass capacitor is connected to the battery during the charging cycle such that charge is accumulated in the bypass capacitor, wherein the delivery capacitor is also charged during the charging cycle based on the charge in the at least one bypass capacitor, and wherein the controller further controls the converter to disconnect the at least one bypass capacitor from the battery after completion of the charging cycle to reduce undesired dissipation of battery energy as a result of leakage currents during the quiescent period of the converter;

wherein the converter comprises a transformer having a primary winding and a secondary winding wherein the switching network periodically connects the battery and the at least one bypass capacitor to the primary winding of the transformer so as to produce changing current in the primary winding that results in inductively induced changing current in the secondary winding and wherein the at least one delivery capacitor is connected to the secondary winding of the transformer such that the changing current results in the delivery of charge to the at least one delivery capacitor;

wherein the switching network comprises a first switching element that is interposed between the at least one bypass capacitor, the battery and the primary winding of the transformer and wherein the controller induces the delivery of a high frequency signal to the first switching element so as to periodically connect the at least one bypass capacitor and the battery in parallel to the primary winding of the transformer;

wherein the switching network further comprises a second switching element that connects the at least one bypass capacitor to the battery wherein the controller induces the second switching element to disconnect the at least one bypass capacitor from the battery during the quiescent periods of the converter;

wherein the first and second switching elements comprise transistors having gates and wherein the controller applies an oscillating signal to the first transistor; and a rectifying element that is interposed between the source of the oscillating signal and the second transistor such that when the oscillating signal is produced, the second transistor receives a substantially constant input voltage that turns on the transistor.

4. The device of claim 3, wherein the implantable delivery device comprises at least one lead adapted to be implanted adjacent the heart of a patient so as to permit the delivery of high voltage therapeutic waveforms to the heart of the patient.

5. The device of claim 3, further comprising a dissipation element that is interposed between the rectifying element and the battery such that, when the oscillating signal is not produced, the voltage on the gate of the transistor is turned off more quickly as a result of the voltage being dissipated through the dissipation element.

6. The device of claim 5, wherein the rectifying element comprises a zener diode and the dissipation element comprises a resistor.

7. The device of claim 3, wherein the at least one bypass capacitor comprises a plurality of ceramic capacitors and the at least one delivery capacitor comprises a plurality of electrolytic capacitors.

8. The device of claim 3, wherein the at least one bypass capacitor is a high frequency filter.

9. An implantable cardiac stimulation device comprising:

at least one lead adapted to be positioned adjacent the heart of the patient to thereby permit delivery of a high voltage therapeutic signal;

a battery that produces a low voltage output;

a converter that comprises at least one bypass capacitor and at least one delivery capacitor, wherein the converter in a charging cycle receives the low voltage output of the battery and charges the at least one bypass capacitor, wherein the at least one bypass capacitor has a capacitance on the order of 20–50 microfarads, and wherein charge is periodically delivered to the at least one delivery capacitor during the charging cycle such that the at least one delivery capacitor is charged to be able to deliver the high voltage therapeutic signal;

a controller that determines the state of charge of the at least one delivery capacitor and induces the converter to enter the charging cycle when the controller determines that the at least one delivery capacitor is in need of charge to be able to deliver the high voltage therapeutic signal and wherein the controller disconnects the at least one bypass capacitor from the battery when the controller determines that the at least one delivery capacitor is not in need of charge to thereby inhibit undesired dissipation of battery energy as a result of leakage currents in the at least one bypass capacitor;

wherein the converter comprises a transformer having a primary winding and a secondary winding wherein the battery and the at least one bypass capacitor are periodically connected to the primary winding of the transformer so as to produce changing current in the primary winding that results in inductively induced changing current in the secondary winding and wherein the at least one delivery capacitor is connected to the secondary winding of the transformer such that the changing current results in the delivery of charge to the at least one delivery capacitor;

wherein the converter comprises a first switching element that is interposed between the at least one bypass capacitor, the battery and the primary winding of the transformer and wherein the controller induces the delivery of an alternating signal to the first switching element so as to periodically connect the at least one bypass capacitor and the battery to the primary winding of the transformer;

wherein the converter further comprises a second switching element that connects the at least one bypass capacitor to the battery wherein the controller induces the second switching element to disconnect the at least one bypass capacitor from the battery when the converter is not in the charging cycle;

wherein the first and second switching elements comprise transistors and wherein the controller induces the application of the alternating signal to the first transistor; and a rectifying element that is interposed between the source of the alternating signal and the second transistor such that when the alternating signal is produced, the second transistor receives a substantially constant input voltage that turns on the second transistor.

10. The device of claim 9, further comprising a dissipation element that is interposed between the rectifying element and the battery such that when the alternating signal is not produced, the voltage on the gate of the second transistor is turned off more quickly as a result of the voltage being dissipated through the dissipation element.

11. The device of claim 10, wherein the rectifying element comprises a zener diode and the dissipation element comprises a resistor.

12. The device of claim 9, wherein the at least one bypass capacitor comprises a plurality of ceramic capacitors and the at least one delivery capacitor comprises an electrolytic capacitor.

13. The device of claim 9, wherein the at least one bypass capacitor is a high frequency filter.

* * * * *